United States Patent
Chan et al.

(10) Patent No.: US 6,680,385 B2
(45) Date of Patent: Jan. 20, 2004

(54) CATALYTIC PREPARATION OF ARYL METHYL KETONES USING A MOLECULAR OXYGEN-CONTAINING GAS AS THE OXIDANT

(75) Inventors: Albert Sun-Chi Chan, Kowloon (HK); Jian-Ying Qi, Kowloon (HK); Cheng-Chao Pai, Kowloon (HK); Xian-Jun Li, Chengdu (CN); Li-Sheng Deng, Chengdu (CN); Wen-Zao Li, Chengdu (CN); Bin Sun, Chengdu (CN); Jia-Yuan Hu, Chengdu (CN)

(73) Assignees: The Hong Kong Polytechnic University, Kowloon (HK); Sichuan University, Chengdu (CN)

( * ) Notice: Subject to any disclaimer, the term of this patent is extended or adjusted under 35 U.S.C. 154(b) by 10 days.

(21) Appl. No.: 10/055,016

(22) Filed: Jan. 25, 2002

(65) Prior Publication Data

US 2003/0144554 A1 Jul. 31, 2003

(51) Int. Cl.⁷ .................. C07D 239/02; C07F 9/00; C07C 211/00; C07C 205/00

(52) U.S. Cl. .............. 544/301; 544/329; 544/334; 556/42; 556/45; 556/57; 564/305; 564/334; 568/306; 568/320; 568/321; 568/328

(58) Field of Search ............... 568/306, 320, 568/321, 328; 564/305, 336; 544/301, 329, 334; 556/42, 45, 57

(56) References Cited

U.S. PATENT DOCUMENTS 4,839,323 A * 6/1989 Goe et al.

* cited by examiner

*Primary Examiner*—Johann Richter
*Assistant Examiner*—Sikarl A. Witherspoon
(74) *Attorney, Agent, or Firm*—Leydig, Voit & Mayer, Ltd.

(57) ABSTRACT

A method for the preparation of aryl methyl ketones converts a variety of ethyl arenas to the corresponding aryl methyl ketones using a dioxygen-containing gas as the oxidant. The catalyst used for the reaction is a metal complex bearing general formulas as disclosed.

30 Claims, No Drawings

CATALYTIC PREPARATION OF ARYL METHYL KETONES USING A MOLECULAR OXYGEN-CONTAINING GAS AS THE OXIDANT

BACKGROUND OF THE INVENTION

1. Field of the Invention

The invention relates to the preparation and application of a new class of metal complexes whose general formula are depicted below:

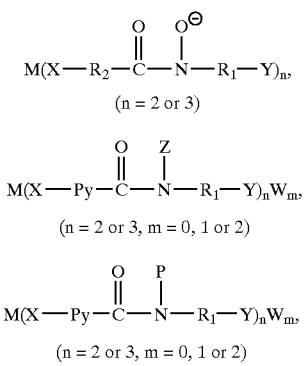

$$M(X-R_2-\underset{\underset{O}{\|}}{C}-\underset{\underset{O^{\ominus}}{|}}{N}-R_1-Y)_n, \quad I$$
(n = 2 or 3)

$$M(X-Py-\underset{\underset{O}{\|}}{C}-\underset{\underset{Z}{|}}{N}-R_1-Y)_nW_m, \quad II$$
(n = 2 or 3, m = 0, 1 or 2)

$$M(X-Py-\underset{\underset{O}{\|}}{C}-\underset{\underset{P}{|}}{N}-R_1-Y)_nW_m, \quad III$$
(n = 2 or 3, m = 0, 1 or 2)

wherein $R_1$ represents substituted and nonsubstituted phenyl (Ph), pyridyl, pyrimidinyl, pyrazinyl, pyrrolyl, pyrrolinyl, imidazolyl, naphthyl, quinolyl, isoquinolyl, quinazolinyl, quinoxalinyl, indenyl, indolyl, 4-isobenzazolyl, indoleninyl, anthracyl, phenanthrolinyl or pyrrolidyl, piperidyl, cycloalkyl groups or any combination thereof. $R_2$ represents substituted and nonsubstituted phenyl (Ph), naphthyl, anthracyl, indenyl, cycloalkyl groups or any combination thereof. Py represents substituted and nonsubstituted pyridyl, pyrimidinyl, pyrazinyl, pyrrolyl, pyrrolinyl, imidazolyl, quinolyl, isoquinolyl, quinazolinyl, quinoxalinyl, indolyl, 4-isobenzazolyl, indoleninyl, phenanthrolinyl, pyrrolidyl, piperidyl or any combination thereof. X and Y can be the same or different, and represent hydrogen (H), hydroxyl (OH), alkyl (R), alkoxy (RO), cycloalkyl, halogen, nitro groups or any combination thereof. Z represents a hydroxyl (OH) or negative oxygen ion (O−). W represents an anion such as a halide, nitrate, sulfate, acetate, trifluoroacetate, trifluoromethanesulfonate, tetrafluoroborate, hexafluorophosphorate, perchlorate, oxalate, carbonate or any combination thereof. P represents a hydrogen atom (H) or negative charge (⊖). M represents a metal ion from groups IB, VB, VIB, VIIB or VIII of the periodic table of the elements. This invention also relates the preparation of aryl methyl ketones via oxidation of ethyl arenes using one of these complexes as catalyst, and using molecular oxygen as oxidant. The improved aryl methyl ketone selectivity and improved conversion of ethyl arene provided by this invention are particularly suitable for the industrial scale production of alkyl aryl ketone compounds.

2. Prior Art

There are several methods for preparing aryl methyl ketones. Among them, the preparation of the structurally simplest acetophenone, which is produced commercially on a large scale, has been most extensively studied. The most commonly used method of preparing acetophenone is via the oxidation of ethylbenzene using cobalt acetate or cobalt cycloalkanecarboxylate type compounds as catalyst, bromide compounds as a co-catalyst in acetic acid solvent, and molecular oxygen or air as the oxidant. A significant disadvantage of this method is the strongly corrosive nature of the bromide compounds and the acetic acid solvent. This type of reaction usually requires the use of expensive corrosion-resistant equipment. Another disadvantage of this method is the low effective utilization of the reactor due to the involvement of a large quantity of the acetic acid solvent. The third disadvantage of this method is the high cost associated with the separation and recycling of the acetic acid solvent.

Yasutaka Ishii (Journal of Molecular Catalysis A: Chemical 117, pp 123–137, 1997) reported a method for the oxidation of ethylbenzene to acetophenone by using N-hydroxyphthalimide as a catalyst, cobalt acetoacetonate as the co-catalyst, and molecular oxygen as the oxidant. The acetophenone product was obtained with high yield. However, this reaction still needed to use acetic acid as solvent, and therefore had corrosion problem. The amount of co-catalyst used in the reaction system was very high (10%), thus making the catalyst system expensive.

Lei et al. reported a method for oxidizing alkyl benzene in the absence of solvent (Chinese Chemical Letters Vol. 3, No. 4, pp 267–268, 1992). In this reaction 2,2'-bipyridyl coordinated ruthenium complex was used as catalyst, and molecular oxygen or air was used as oxidant. The highest ethylbenzene conversion was only 43.8%, and the selectivity for acetophenone was only 74%.

Lei et al. also reported another method for oxidizing alkyl benzene (Chinese Chemical Letters Vol. 4, No. 1, pp 21–22, 1993) without the use of any solvent. The method employed Fe-(2,2'-bipyridyl) or Fe-(1,10-phenanthroline) as the catalyst and molecular oxygen as oxidant. When 5 mL of ethylbenzene was oxidized in the presence of 2 mg of the catalyst, the conversion of ethylbenzene was only 11.4–34.6% after 3.5 hours. The selectivity for acetophenone was only 66.2–89.8%.

When using either one of Lei's methods to prepare acetophenone, one cannot get both high turnover frequency and good acetophenone selectivity. Taking the best result from Chinese Chemical Letters Vol. 4, No.1, pp 21–22, 1993 as an example, when the conversion of ethylbenzene was 25.3% (turnover frequency 686 mol/mol catalyst-hour), the selectivity for acetophenone was 89.8%. However, the selectivity for acetophenone dropped to 67.22% when the ethylbenzene conversion was increased to 34.58% (turnover frequency 1010 mol/mol catalyst·hour). Among the reported methods for substituted ethylbenzene oxidation and the oxidation of other ethyl arenes (such as the oxidation of halo-ethylbenzene, methyl-ethylbenzene, methoxy-ethylbenzene, nitro-ethylbenzene or ethyl-naphthalene, etc.), normally a peroxide compound was used as the oxidant. The use of molecular oxygen as oxidant has not been reported.

OBJECT OF THE INVENTION

It is an object of the present invention to overcome or a substantially ameliorate at least one of the above disadvantages.

It is another object of the present invention is to provide a highly effective method for the selective preparation of methyl aryl ketones via the oxidation of ethyl arenas using molecular oxygen as the oxidant without the use of any solvent.

SUMMARY OF THE INVENTION

This invention provides the methods for the preparation of three classes of complexes with the general formula shown below:

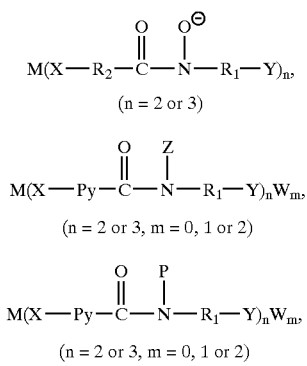

(n = 2 or 3)  I (n = 2 or 3, m = 0, 1 or 2)  II (n = 2 or 3, m = 0, 1 or 2)  III

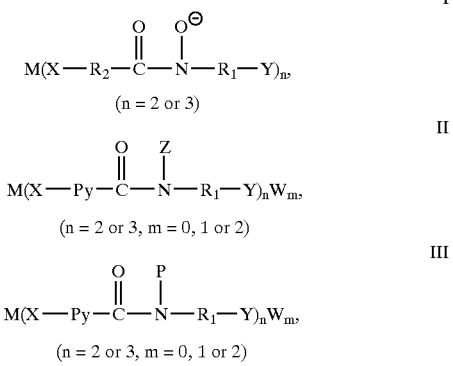

(n = 2 or 3)  I (n = 2 or 3, m = 0, 1 or 2)  II (n = 2 or 3, m = 0, 1 or 2)  III wherein $R_1$ represents substituted and nonsubstituted phenyl (Ph), pyridyl, pyrimidinyl, pyrazinyl, pyrrolyl, pyrrolinyl, imidazolyl, naphthyl, quinolyl, isoquinolyl, quinazolinyl, quinoxalinyl, indenyl, indolyl, 4-isobenzazolyl, indoleninyl, anthracyl, phenanthrolinyl or pyrrolidyl, piperidyl, cycloalkyl groups or any combination thereof $R_2$ represents substituted and nonsubstituted phenyl (Ph), naphthyl, anthracyl, indenyl, cycloalkyl groups or any combination thereof. Py represents substituted and nonsubstituted pyridyl, pyrimidinyl, pyrazinyl, pyrrolyl, pyrrolinyl, imidazolyl, quinolyl, isoquinolyl, quinazolinyl, quinoxalinyl, indolyl, 4-isobenzazolyl, indoleninyl, phenanthrolinyl, pyrrolidyl, piperidyl or any combination thereof. X and Y can be the same or different, and represent hydrogen (H), hydroxyl (OH), alkyl (R), alkoxy (RO), cycloalkyl, halogen, nitro groups or any combination thereof. Z represents a hydroxyl (OH) or negative oxygen ion (O$^-$). W represents an anion such as a halide, nitrate, sulfate, acetate, trifluoroacetate, trifluoromethanesulfonate, tetrafluoroborate, hexafluorophosphorate, perchlorate, oxalate, carbonate or any combination thereof. P represents a hydrogen atom (H) or negative charge (⊖). M represents a metal ion from groups IB, VB, VIB, VIIB or VIII of the periodic table of the elements.

This invention also includes the use of these complexes as catalysts for oxidizing ethyl arenes to aryl methyl ketones. The catalysts have the advantages of high ethyl arene conversion, high turnover frequency as well as high selectivity for the aryl methyl ketone products.

DETAILED DESCRIPTION OF THE PREFERRED EMBODIMENTS OF THE INVENTION

The purpose of this invention is to provide a method for the selective preparation of methyl aryl ketone via oxidation of ethyl arene using molecular oxygen as the oxidant without the use of any solvent.

The method of the preferred embodiment includes carrying out the reaction at 50–300° C. at any pressure between atmospheric pressure and 10 MPa, and reacting ethyl arene with a catalyst and an oxygen-containing gas such as air or oxygen-enriched air. The concentration of the catalyst in the reaction system is in a range from $10^{-6}$ to 5.0 mol/L, and the catalyst is a complex of the following general formula or a mixture of these species:

wherein $R_1$ represents substituted and nonsubstituted phenyl (Ph), pyridyl, pyrimidinyl, pyrazinyl, pyrrolyl, pyrrolinyl, imidazolyl, naphthyl, quinolyl, isoquinolyl, quinazolinyl, quinoxalinyl, indenyl, indolyl, 4-isobenzazolyl, indoleninyl, anthracyl, phenanthrolinyl or pyrrolidyl, piperidyl, cycloalkyl groups or any combination thereof. $R_2$ represents substituted and nonsubstituted phenyl (Ph), naphthyl, anthracyl, indenyl, cycloalkyl groups or any combination thereof. Py represents substituted and nonsubstituted pyridyl, pyrimidinyl, pyrazinyl, pyrrolyl, pyrrolinyl, imidazolyl, quinolyl, isoquinolyl, quinazolinyl, quinoxalinyl, indolyl, 4-isobenzazolyl, indoleninyl, phenanthrolinyl, pyrrolidyl, piperidyl or any combination thereof. X and Y can be the same or different, and represent hydrogen (H), hydroxyl (OH), alkyl (R), alkoxy (RO), cycloalkyl, halogen, nitro groups or any combination thereof. Z represents a hydroxyl (OH) or negative oxygen ion (O$^-$). W represents an anion such as a halide, nitrate, sulfate, acetate, trifluoroacetate, trifluoromethanesulfonate, tetrafluoroborate, hexafluorophosphorate, perchlorate, oxalate, carbonate or any combination thereof. P represents a hydrogen atom (H) or negative charge (⊖). M represents a metal ion from groups IB, VB, VIB, VIIB or VIII of the periodic table of the elements. The invention also includes the preparation of these catalysts. This invention also relates the preparation of aryl methyl ketones via oxidation of ethyl arenes using one of these complexes as catalyst and molecular oxygen as the oxidant. The improved aryl methyl ketone selectivity and improved conversion of ethyl arene provided by this invention are particularly suitable for the industrial scale preparation of aryl ketone compounds.

When X=Y=H, $R_1$=$R_2$=Ph, the ligand in complex (I) is N-phenylbenzohydroxamic acid, abbreviated as HPBHA, and the complex in general formula (I) is N-phenylbenzohydroxamate anion coordinated M complex, abbreviated as M(PBHA)$_n$. PBHA represents the deprotonated form of HPBHA.

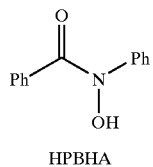

HPBHA

When X=Y=H, $R_1$=Ph, Py=pyridyl, Z=OH, and the carbonyl group is at the ortho, meta or para-position relative to the pyridine nitrogen atom, the ligand in the general formula (II) is N-phenyl-2-pyridinecarbonylhydroxamic acid, N-phenyl-3-pyridinecarbonylhydroxamic acid or N-phenyl- 4-pyridinecarbonylhydroxamic acid, abbreviated as o-HPPHA, m-HPPHA or p-HPPHA, respectively. The complex in general formula (II) is N-phenyl-2-pyridinecarbonylhydroxamate anion coordinated M complex, abbreviated as M(o-PPHA)$_n$, N-phenyl-3-pyridinecarbonylhydroxamate anion coordinated M complex, abbreviated as M(m-PPHA)$_n$ or N-phenyl-4-pyridinecarbonylhydroxamate anion coordinated M complex, abbreviated as M(p-PPHA)$_n$. PPHA represents the deprotonated form of HPPHA.

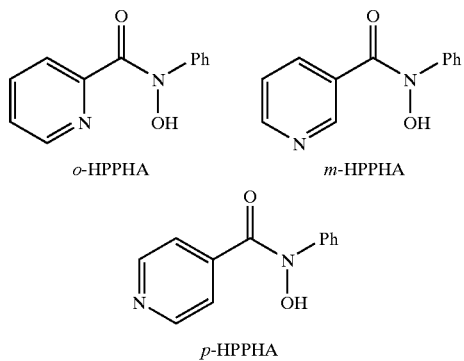

In this invention, the X group in the general formula (II) and (III) can be at any possible position in the pyridine ring, that is, the 3-, 4-, 5- or 6-position of the pyridine ring.

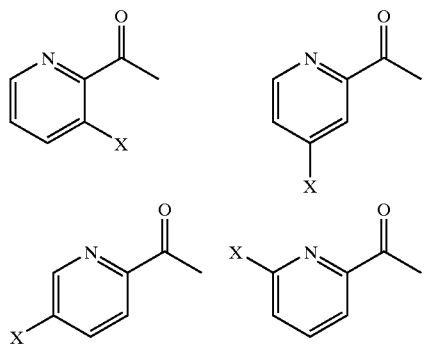

When X=Y=P=H, R$_1$=Ph, Py=2-pyridyl, the ligand in general formula (III) is N-phenyl-2-pyridinecarboxamide, and is abbreviated as HPPA or its deprotonated anion form PPA. The complex in general formula (III) is N-phenyl-2-pyridinecarboxamide or its anion coordinated M complex, and is abbreviated as M(PPA)$_n$ (M=Co, n=3; M=Cu, n=2), M(HPPA)(PPA)$_2$ (M=Ni), M(HPPA)$_2$W$_2$ (M=Mn, W=Cl) or M(HPPA)(PPA)W$_2$ (M=Ru, W=Cl) etc.

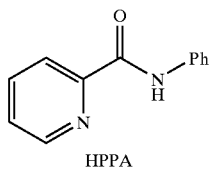

HPPA

This description of certain particular catalyst formulae is by no means intended to limit the scope of this invention to the specific complexes so described. Any complex meeting the general description claimed above is within the scope of this invention.

The catalyst used in this invention can be prepared according to the following procedure, which is presented as an example only. Any other similar procedures also fall within the scope of this invention:

(1) The preparation of catalyst of general structure (I): A ligand in general structure (I) is dissolved in an alcohol solvent so that the concentration of the ligand is from $10^{-3}$ to 1.0 mol/L. A suitable concentration is from 0.05 to 0.5 mol/L. With the temperature at 20 to 150° C. (most favorable temperature is 40 to 100° C.), a solution containing metal ion M with the concentration of $10^{-2}$ to 1.0 mol/L (the most favorable concentration is 0.1 to 0.4 mol/L) is added to the ligand solution. The amount of metal ion is such that it makes the ligand-to-metal molar ratio in a range of 1 to 5 (most favorable ratio is in a range of 2 to 3). The precipitate is filtered off and the solid is washed with de-ionized water until it is free of acid. A complex of general structure (I) can thus be obtained.

The alcohol can be any aliphatic alcohol of $C_1$–$C_5$, for example, methanol, ethanol, n-propanol, i-propanol, all the isomers of butanol, and all the isomers of pentanol. Among these, the more favorable are ethanol or n-propanol and the most favorable is ethanol.

The metal ion solution is an aqueous or alcoholic solution of a soluble salt of metal. For example, the aqueous or alcoholic solution of a metal halide, nitrate, sulfate, acetate, trifluoroacetate, trifluoromethanesulfonate, tetrafluoroborate, hexafluorophosphorate, perchlorate, oxalate, carbonate or any combination thereof.

The temperature for drying the complex is from room temperature to 200° C. and the most favorable temperature range is 80 to 150° C.

(2) The preparation of catalyst of general structure (II): the ligand for preparing the complex is dissolved in alcohol to give a solution concentration of about 0.02 to 2 mol/L (The more favorable concentration range is 0.05 to 1.0 mol/L). The alcoholic or aqueous solution containing M ion is added at 10 to 150° C. (preferably at 40 to 100° C.) with stirring. The mixture is reacted for 0.2 to 5 hours (preferably 0.5 to 3 hours). The concentration of the M ion in the stock solution is about 0.05 to 2 mol/L (preferably 0.1 to 1.0 mol/L). The amount of added M ion is such that the molar ratio of ligand-to-metal ion is between 1:1 and 4:1 (preferably between 2:1 and 3:1). The precipitate thus formed is filtered off, washed with 95% alcohol until it is acid-free, and dried to give a complex of general structure (II).

The alcohol in the above mentioned preparation can be any aliphatic alcohol of $C_1$ to $C_5$, such as methanol, ethanol, n-propanol, i-propanol, all isomers of butanol, and all isomers of pentanol. The more favorable are ethanol or propanol, and the most favorable alcohol is ethanol.

The alcoholic or aqueous solution of the metal ion may be the alcoholic or aqueous solution of the metal salt, such as the alcoholic solution of a metal halide, nitrate, sulfate, acetate, trifluoroacetate, trifluoromethanesulfonate, tetrafluoroborate, hexafluorophosphorate, perchlorate, oxalate, carbonate or any combination thereof.

The temperature for drying the ligand is room temperature to 180° C. (preferably 50 to 150° C.).

(3) The preparation of catalyst of general formula (III): the ligand for preparing the complex is dissolved in an alcohol to make a solution of a concentration in a range of 0.05 to 2 mol/L (preferably 0.1 to 1.0 mol/L). An aqueous solution containing M ion and ammonia is added with stirring and reacted for 0.5 to 4 hours (preferably 1 to 2 hours). In the aqueous or alcoholic solution of metal ion and ammonia, the concentration of metal ion is 0.02 to 2 mol/L (preferably 0.05 to 1.0 mol/L). The metal ion concentration is such that the molar ratio of ligand to metal ion is between 1:1 and 5:1 (preferably between 2:1 and 3:1). The concentration of ammonia is 0.1 to 30 mol/L (preferably 0.5 to 10 mol/L). The thus formed precipitate was filtered off, washed until it is acid free using de-ionized water, and dried to give a complex of general formula (III).

The alcohol in the above mentioned preparation can be any aliphatic alcohol of $C_1$ to $C_5$, such as methanol, ethanol, n-propanol, i-propanol, all isomers of butanol, and all isomers of pentanol. The more favorable are ethanol or propanol, and the most favorable alcohol is ethanol.

The mixed aqueous or alcoholic solution of metal ion and ammonia can be made from any soluble salt of the metal ion, such as metal halide, nitrate, sulfate, acetate, trifluoroacetate, trifluoromethanesulfonate, tetrafluoroborate, hexafluorophosphorate, perchlorate, oxalate, carbonate or thereof, and aqueous ammonia.

The temperature for drying the product is room temperature to 200° C. (preferably 70 to 150° C.).

In this invention, the catalyst concentration in the reaction system is $10^{-6}$ to 5.0 mol/L (preferably $10^{-5}$ to $10^{-2}$ mol/L).

The reaction temperature is 50 to 300° C. (preferably 100 to 150° C.).

The oxygen pressure in the reactor can be ambient pressure to 10 MPa, but for economic reason preferably ambient pressure to 3 MPa, and most preferably ambient to 1.5 MPa.

The reaction time varies with the variation of the catalyst concentration, reaction temperature and reaction pressure higher reaction temperature gives faster turnover frequency and the reaction requires shorter time to reach a specific conversion level. The turnover frequency is higher under higher reaction pressure. Higher turnover frequency and shorter reaction time needed to reach a specific conversion is also achieved by using higher catalyst concentration. For the convenience of operation, the usual reaction time is in a range of 0.5 to 20 hours, typically 2 to 12 hours.

The oxygen-containing gas used in the reaction may be pure oxygen or a gas containing $O_2$ such as air or oxygen-enriched air with other gaseous contents that do not affect the reaction. The oxygen content of the oxygen-containing gas should be above 20% (V/V) or higher. The other gaseous contents, which do not affect the reaction, may include the group 0 inert gases of the periodic table, nitrogen or carbon dioxide or any mixture of them. The preferable oxygen-containing gases are pure oxygen, oxygen-enriched air or air.

In the preferred embodiment, the ethyl arene is any arene bearing an ethyl group as a substituent on the aromatic ring. For example, substituted or unsubstituted ethylbenzene or ethylnaphthalene. The favorable ethylarenes include ethylbenzene, ethylnaphthalene, substituted ethylbenzene or ethylnaphthalene bearing one or several halo, methyl, methoxy, nitro group or any combination of thereof as the substituent. They are oxidized to acetophenone, halo acetophenone, methyl acetophenone, methoxy acetophenone, nitro acetophenone, methyl naphthyl ketone or any methyl aryl ketone bearing any combination of the substitutes. The more favorable ethyl arenes include ethylbenzene, halo ethylbenzene or methoxy ethylbenzene.

In this preferred embodiment, the catalyst can be readily separated from the reaction system through distillation of the reaction mixture, and the separated catalyst can be recycled and reused.

Compared with previously known solvent free methods, the method of this invention can give higher conversion of ethylarene and high yield of the desired methyl aryl ketone product. For example, using ethylbenzene to produce acetophenone, acetophenone selectivity can be as high as 93% even when the ethylbenzene conversion is as high as 63%.

In addition, high acetophenone selectivity can still be obtained even when running the reaction at high turnover frequency. For example, using the method in this invention, acetophenone selectivity can be 90% when the turnover frequency is as high as about 1500 mol/mol catalyst-hour.

EXAMPLE 1

Preparation of $Co(PPA)_3$ catalyst (1) 2-pyridinecarboxylic acid (2.46 g, 20 mmol) and 20 mL of $SOCl_2$ were added to a three necked flask and the reaction mixture was refluxed for 2 hours. 2-pyridinecarboxylic chloride was obtained after the $SOCl_2$ was washed off with benzene.

(2) 2-pyridinecarbonyl chloride (2.54 g, 18 mmol) and aniline (1.86 g, 20 mmol) were added to 40 mL of anhydrous tetrahydrofuran and the mixture was reacted at 50° C. for 2 hours. After cooling, the mixture was neutralized to pH=7 and was filtered. The solid was washed with 20 mL distilled water three times. HPPA ligand (3.39 g) was obtained after drying.

(3) HPPA (325 mg, 1.52 mmol) was dissolved in 15 mL of ethanol, to which 5 mL of an aqueous solution containing $CoCl_2.6H_2O$ (181 mg, 0.76 mmol) and 3 mL 25% ammonia was added with stirring at 45° C. After reacting for 1 hour, the precipitate was filtered off, washed with de-ionized water until chloride ion-free (identified by 0.1 mol/L $AgNO_3$), and was dried at 100° C. $Co(PPA)_3$ catalyst (412 mg) was obtained.

EXAMPLES 2–3

Catalyst $Ni(HPPA)(PPA)_2$ and $Cu(PPA)_2$ were prepared using methods similar to those in example 1, and aqueous nickle chloride and copper sulfate were used in place of cobalt chloride. The reaction time was 2 hours and 3 hours, for the Ni and Cu complexes, respectively.

EXAMPLE 4

Catalyst $Mn(HPPA)_2Cl_2$ was prepared using methods similar to those in example 1, except that no ammonia was added, and aqueous manganese dichloride was used in place of cobalt chloride. The reaction time was 2 hours.

EXAMPLE 5

Preparation of $Co(PBHA)_2$ catalyst (1) Preparation of N-hydroxylaniline:
To a mixture of 10 g of nitrobenzene, 1.2 g of ammonium chloride and 80 mL water (the molar concentration of nitrobenzene was 1.0 mol/L, the weight ratio of nitrobenzene to ammonium chloride was 8.3:1) was added 15 g of zinc dust (the molar ratio of zinc to nitrobenzene was 1.5) and the reaction was carried out at 70° C. for 4 hours to reduce the nitrobenzene. The zinc oxide formed was filtered off and the solid was washed with 20 mL of distilled water twice. The filtrate was saturated with sodium chloride and the precipitated solid was filtered off and dried to give N-hydroxylaniline.

(2) Preparation of the ligand HPBHA:
To 30 mL of anhydrous tetrahydrofuran solution containing 31.8 g of sodium carbonate was added a mixture of benzoyl chloride (1.1 g, 8 mmol) and N-hydroxylaniline (0.9 g, 8 mmol). The reaction was carried out at −5° C. for 3 hours. The solution was treated with sodium bicarbonate (63 g/L, 0.5 mol/L) to pH=8. The resulting solid was dried at 100° C. to give HPBHA.

(3) Preparation of Co(PBHA)$_2$ catalyst:

HPBHA (256 mg, 1.2 mmol) was dissolved in 15 mL of ethanol. With stirring, 6 mL of an aqueous cobalt chloride solution (23.8 g/L, 0.1 mol/L) was added to this solution at 50° C. and the reaction was allowed to continue for 2 hours. The molar ratio of ligand to Co was 2:1. The resulting precipitate was filtered off and was washed with de-ionized water until free of chloride ion, followed by drying at 100° C. to give 290 mg of Co(PBHA)$_2$ catalyst.

EXAMPLE 6

Preparation of Co(o-PPHA)$_2$ catalyst (1) 2-pyridinecarbonyl chloride was prepared according to the procedure described in step (1) of example 1.

(2) Preparation of o-HPPHA:

To an anhydrous tetrahydrofuran solution containing 64 g/L of sodium carbonate was added a mixture of 2-pyridinecarbonyl chloride (2.82 g, 20 mmol) and N-hydroxylaniline (5.21 g, 23 mmol). The reaction was carried out at −5° C. for 2.5 hours. The solid was filtered off and was washed with 20 mL of saturated aqueous sodium bicarbonate twice, then washed with distilled water until the washing became neutral. The solid was then dried at 100° C. to give 2.10 g of o-HPPHA.

(3) Preparation of Co(o-PPHA):

o-HPPHA (235 mg, 1.1 mmol) was dissolved in 15 mL of ethanol. With stirring, cobalt chloride (119 mg, 0.5 mmol) in 5 mL ethanol was added to this solution at 50° C. and the reaction was continued for 2 hours. The resulting precipitate was filtered and was washed with 95% ethanol (w/w) until the washing is free of chloride ion, followed by drying at 110° C. to give 134 mg of Co(o-PPHA)$_2$.

EXAMPLE 7

The following is an example of the synthetic application of this invention.

To a 250 mL autoclave was added 100 mL of ethylbenzene and 26 mg Co(PPA)$_3$ catalyst prepared according to the method in example 1. The autoclave was charged with oxygen to maintain the oxygen pressure at 0.1 MPa. The reaction was carried out at 130° C. for 6 hours, and the reaction mixture was analyzed via gas chromatography (GC). The analysis showed that the conversion of ethylbenzene was 40.5% and the selectivity for acetophenone was 92.5%. The turnover frequency was 1379 mol/mol catalyst·hour.

Ethylbenzene conversion=(moles of ethylbenzene converted/initial moles of the starting ethylbenzene)×100%;

Acetophenone selectivity=(moles of the acetophenone formed/moles of ethylbenzene converted)×100%;

Turnover frequency refers to the moles of ethylbenzene converted every hour divided by the number of moles of the catalyst.

EXAMPLE 8

To a 250 mL autoclave was added 100 mL of ethylbenzene and 10 mg of Co(PBHA)$_2$ catalyst. The autoclave was then charged with oxygen to maintain the oxygen pressure at 0.8 MPa. The reaction was carried out at 140° C. for 8 hours, and the resulting reaction mixture was analyzed by GC. The analysis showed that the conversion of ethylbenzene was 39.8% and the selectivity for acetophenone was 87.3%. The turnover frequency was 2032 mol/mol catalyst·hour.

EXAMPLE 9

Acetophenone was prepared using a procedure similar to that described in example 8, except that the concentration of the Co(PBHA)$_2$ catalyst was 20 mg, the reaction temperature was 130° C. and the reaction time was 6 hours. The ethylbenzene conversion was 43.0%, the selectivity for acetophenone was 82.0%. The turnover frequency was 1463 mol/mol catalyst·hour.

EXAMPLE 10

To a 100 mL autoclave was added 20 mL of ethylbenzene and 13 mg Co(PPA)$_3$ catalyst. The autoclave was charged with oxygen to maintain the oxygen pressure at 0.6 M Pa. The reaction was carried out at 140° C. for 6 hours, and the resulting mixture was analyzed by GC. The analysis showed that the conversion of ethylbenzene was 50.5%, and the selectivity for acetophenone was 90.9%. The turnover frequency was 1822 mol/mol catalyst·hour.

EXAMPLE 11

To a 100 mL autoclave was added 20 mL of ethylbenzene and 10 mg Co(o-PPHA)$_2$ catalyst. The autoclave was charged with oxygen to maintain the oxygen pressure at 0.8 MPa. The reaction was carried out at 130° C. for 6 hours, and the resulting reaction mixture was analyzed by GC. The analysis showed that the conversion of ethylbenzene was 64.0%, and the selectivity for acetophenone was 81.4%. The turnover frequency was 2309 mol/mol catalyst·hour.

EXAMPLE 12

To a 100 mL autoclave was added 20 mL of ethylbenzene and 5.2 mg Ni(HPPA)(PPA)$_2$ catalyst. The autoclave was charged with oxygen to maintain the oxygen pressure at 1.0 MPa. The reaction was carried out at 130° C. for 8 hours, and the resulting reaction mixture was analyzed by GC. The analysis showed that the conversion of ethylbenzene was 35.8%, and the selectivity for acetophenone was 85.3%. The turnover frequency was 968 mol/mol catalyst·hour.

EXAMPLE 13

Acetophenone was prepared as described in example 12, except that the catalyst used in that example was replaced by 4.1 mg Mn(HPPA)$_2$Cl$_2$. The autoclave was charged with oxygen to maintain the oxygen pressure at 1.0 MPa. The conversion of ethylbenzene was 35.1%, the selectivity for acetophenone was 88.2%. The turnover frequency was 949 mol/mol catalyst·hour.

EXAMPLE 14

To a 100 mL autoclave was added 10 mL of o-bromo-ethylbenzene and 14.5 mg Co(PBHA)$_2$ catalyst. The autoclave was charged with oxygen to maintain an oxygen pressure of 0.8 MPa. The reaction was carried out at 140° C. for 8 hours, and the resulting reaction mixture was analyzed by GC. The analysis showed that the conversion of o-bromo-ethylbenzene was 35.9% and the selectivity for o-bromo-acetophenone was 70.4%. The turnover frequency was 80.8 mol/mol catalyst·hour.

o-Bromo-ethylbenzene conversion=(moles of the converted o-bromo-ethylbenzene/the initial moles of o-bromo ethylbenzene)×100%; o-bromo-acetophenone selectivity=(moles of the formed o-bromo-acetophenone/moles of converted o-bromo-ethylbenzene)×100%; turnover frequency refers to the moles of o-bromo-ethylbenzene converted every hour per mole of catalyst present.

EXAMPLE 15

To a 100 mL capacity autoclave was added 10 mL of p-methyl-ethylbenzene and 7.3 mg Co(PBHA)$_2$ catalyst. The autoclave was charged with oxygen to maintain an oxygen pressure of 1.0 MPa. The reaction was carried out at 140° C. for 6 hours, and the resulting reaction mixture was analyzed by GC. The analysis showed that the conversion of p-methyl-ethylbenzene was 58.7% and the selectivity for p-methyl-acetophenone was 76.7%. The turnover frequency was 529 mol/mol catalyst·hour.

p-Methyl-ethylbenzene conversion=(moles of p-methyl-ethylbenzene converted/initial moles of p-methyl-ethylbenzene)×100%; p-methyl-acetophenone selectivity=(moles of the p-methyl-acetophenone formed/moles of p-methyl-ethylbenzene converted)×100%; turnover frequency refers to the moles of p-methyl-ethylbenzene converted every hour per mole of catalyst.

EXAMPLE 16

To a 100 mL capacity autoclave was added 10 mL of p-methyl-ethylbenzene and 6.9 mg Cu(PPA)$_2$ catalyst. The autoclave was charged with oxygen to maintain an oxygen pressure of 1.0 MPa. The reaction was carried out at 140° C. for 8 hours and the resulting reaction mixture was analyzed by GC. The analysis showed that the conversion of p-methyl-ethylbenzene was 42.0% and the selectivity for p-methyl acetophenone was 75.2%. The turnover frequency was 284 mol/mol catalyst·hour.

p-Methyl-ethylbenzene conversion=(moles of p-methyl-ethylbenzene converted/initial moles of p-methyl-ethylbenzene)×100%;

p-methyl-acetophenone selectivity=(moles of p-methyl-acetophenone formed/moles of p-methyl-ethylbenzene converted)×100%;

Turnover frequency refers to the moles of p-methyl-ethylbenzene converted every hour in per mole of catalyst.

EXAMPLE 17

Acetophenone was prepared as described in example 8, except that the oxidant used was air in place of pure oxygen and it was bubbled into the reaction system. The flow rate of the air was 50 mL/min, and the unreacted air escaped through the reactor's cooling condenser. After reacting for 10 hours the reaction system was analyzed with GC. The conversion of ethylbenzene was 31%, the selectivity for acetophenone was 89.1% and the turnover frequency was 1266 mol/mol catalyst·hour.

References

Yasutaka Ishii et al. Journal of Molecular Catalysis A: Chemical 117, pp 123–137, 1997

Lei et al. Chinese Chemical Letters Vol. 3, No. 4, pp 267–268, 1992

Lei et al. Chinese Chemical Letters Vol. 4, No. 1, pp 21–22, 1993

We claim:
1. A complex of the formula:

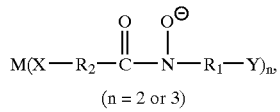

(n = 2 or 3)

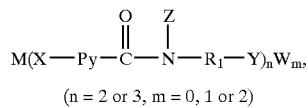

(n = 2 or 3, m = 0, 1 or 2)

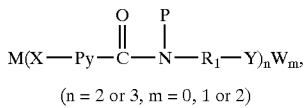

(n = 2 or 3, m = 0, 1 or 2)

wherein:
(a) $R_1$ represents substituted or nonsubstituted phenyl (Ph), pyridyl, pyrimidinyl, pyrazinyl, pyrrolyl, pyrrolinyl, imidazolyl, naphthyl, quinolyl, isoquinolyl, quinazolinyl, quinoxalinyl, indenyl, indolyl, 4-isobenzazolyl, indoleninyl, anthracyl, phenanthrolinyl, pyrrolidyl, piperidyl, cycloalkyl, or any combination thereof;
(b) $R_2$ represents substituted or nonsubstituted phenyl (Ph), naphthyl, anthracyl, indenyl, cycloalkyl, or any combination thereof;
(c) Py represents substituted or nonsubstituted pyridyl, pyrimidinyl, pyrazinyl, pyrrolyl, pyrrolinyl, imidazolyl, quinolyl, isoquinolyl, quinazolinyl, quinoxalinyl, indolyl, 4-isobenzazolyl, indoleninyl, phenanthrolinyl, pyrrolidyl, piperidyl, or any combination thereof;
(d) X and Y can be the same or different, and represent hydrogen (H), hydroxyl (OH), alkyl (R), alkoxy (RO), cycloalkyl, halogen, nitro, or any combination thereof;
(e) Z represents a hydroxyl group (OH) or negative oxygen ion (O$^-$);
(f) W represents an anion such as a halide, nitrate, sulfate, acetate, trifluoroacetate, trifluoromethanesulfonate, tetrafluoroborate, hexafluorophosphorate, perchlorate, oxalate, carbonate, or any combination thereof;
(g) P represents a hydrogen atom (H) or negative charge (⊖); and
(h) M represents a metal ion from group IB, VB, VIB, VIIB or VIII in the periodic table of the elements.

2. The complex of claim 1 having the formula M(PBHA)$_n$ wherein PBHA represents N-phenylbenzohydroxamate.

3. The complex of claim 1 having the formula M(m-PPHA)$_n$ wherein m-PPHA represents N-phenyl-3-pyridinecarbonylhydroxamate anion.

4. The complex of claim 1 having the formula M(p-PPHA)$_n$ wherein p-PPHA represents N-phenyl-4-pyridinecarbonylhydroxamate anion.

5. The complex of claim 1 having the formula M(o-PPHA)$_n$ wherein o-PPHA represents N-phenyl-2-pyridinecarbonylhydroxamate anion.

6. A complex of the formula Co(PPA)$_3$, Cu(PPA)$_2$, Ni(HPPA)(PPA)$_2$, Mn(HPPA)$_2$Cl$_2$, or Ru(HPPA)(PPA)Cl$_2$ wherein HPPA represents N-phenyl-2-pyridinecarboxamide and PPA represents the deprotonated anion form of HPPA.

7. A process for the preparation of an aryl methyl ketone via the oxidation of an ethyl arene using the complex of claim 1 as a catalyst, and molecular oxygen, including pure oxygen or air or oxygen-enriched air, as an oxidant.

8. A process for the preparation of an aryl methyl ketone via the oxidation of an ethyl arene using the complex of claim 2 as a catalyst, and molecular oxygen, including pure oxygen or air or oxygen-enriched air, as an oxidant.

9. A process for the preparation of an aryl methyl ketone via the oxidation of an ethyl arene using the complex of claim 3 as a catalyst, and molecular oxygen, including pure oxygen or air or oxygen-enriched air, as an oxidant.

10. A process for the preparation of an aryl methyl ketone via the oxidation of an ethyl arene using the complex of claim 4 as a catalyst, and molecular oxygen, including pure oxygen or air or oxygen-enriched air, as an oxidant.

11. A process for the preparation of an aryl methyl ketone via the oxidation of an ethyl arene using the complex of claim 5 as a catalyst, and molecular oxygen, including pure oxygen or air or oxygen-enriched air, as an oxidant.

12. A process for the preparation of aryl methyl ketone via the oxidation of an ethyl arene using the complex of claim 6 as a catalyst, and molecular oxygen, including pure oxygen or air or oxygen-enriched air, as an oxidant.

13. The process of claim 7, wherein the catalytic reaction is carried out at 50–300° C. at any pressure between atmospheric pressure and 10 MPa.

14. The process of claim 13, wherein the concentration of the catalyst in the reaction system is from $10^{-6}$ to 5.0 mol/L.

15. The process of claim 14, wherein the ethyl arene includes ethylbenzene, ethylnaphthalene, substituted ethylbenzene, or ethylnaphthalene bearing one to five methyl, methoxyl, nitro, or halo groups or any combination thereof, on the aromatic ring.

16. The process of claim 8, wherein the catalytic reaction is carried out at 50–300° C. at any pressure between atmospheric pressure and 10 MPa.

17. The process of claim 9, wherein the catalytic reaction is carried out at 50–300° C. at any pressure between atmospheric pressure and 10 MPa.

18. The process of claim 10, wherein the catalytic reaction is carried out at 50–300° C. at any pressure between atmospheric pressure and 10 MPa.

19. The process of claim 11, wherein the catalytic reaction is carried out at 50–300° C. at any pressure between atmospheric pressure and 10 MPa.

20. The process of claim 12, wherein the catalytic reaction is carried out at 50–300° C. at any pressure between atmospheric pressure and 10 MPa.

21. The process of claim 16, wherein the concentration of the catalyst in the reaction system is from $10^{-6}$ to 5.0 mol/L.

22. The process of claim 17, wherein the concentration of the catalyst in the reaction system is from $10^{-6}$ to 5.0 mol/L.

23. The process of claim 18, wherein the concentration of the catalyst in the reaction system is from $10^{-6}$ to 5.0 mol/L.

24. The process of claim 19, wherein the concentration of the catalyst in the reaction system is from $10^{-6}$ to 5.0 mol/L.

25. The process of claim 20, wherein the concentration of the catalyst in the reaction system is from $10^{-6}$ to 5.0 mol/L.

26. The process of claim 21, wherein the ethyl arene includes ethylbenzene, ethylnaphthalene, substituted ethylbenzene, or ethylnaphthalene bearing one to five methyl, methoxyl, nitro, or halo groups, or any combination thereof on the aromatic ring.

27. The process of claim 22, wherein the ethyl arene includes ethylbenzene, ethylnaphthalene, substituted ethylbenzene, or ethylnaphthalene bearing one to five methyl, methoxyl, nitro, or halo groups or any combination thereof on the aromatic ring.

28. The process of claim 23, wherein the ethyl arene includes ethylbenzene, ethylnaphthalene, substituted ethylbenzene, or ethylnaphthalene bearing one to five methyl, methoxyl, nitro, or halo groups or any combination thereof on the aromatic ring.

29. The process of claim 24, wherein the ethyl arene includes ethylbenzene, ethylnaphthalene, substituted ethylbenzene, or ethylnaphthalene bearing one to five methyl, methoxyl, nitro, or halo groups or any combination thereof on the aromatic ring.

30. The process of claim 25, wherein the ethyl arene includes ethylbenzene, ethylnaphthalene, substituted ethylbenzene, or ethylnaphthalene bearing one to five methyl, methoxyl, nitro, or halo groups or any combination thereof on the aromatic ring.

* * * * *